(12) United States Patent
O'Shea et al.

(10) Patent No.: US 6,232,472 B1
(45) Date of Patent: May 15, 2001

(54) SYNTHESIS OF 4-[(5-SUBSTITUTED PHENYL)-3-SUBSTITUTED-1H-PYRAZOL-1-YL]BENZENESULFONAMIDE

(75) Inventors: Paul O'Shea, Montreal; Xin Wang, Kirkland, both of (CA); Richard D. Tillyer, Westfield, NJ (US); Sophie-Dorothee Clas; Chad Dalton, both of Montreal (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/660,685

(22) Filed: Sep. 13, 2000

Related U.S. Application Data

(62) Division of application No. 09/483,564, filed on Jan. 14, 2000, now Pat. No. 6,150,534.
(60) Provisional application No. 60/115,834, filed on Jan. 14, 1999.

(51) Int. Cl.[7] .................................................. C07D 231/12
(52) U.S. Cl. ........................................................ 548/377.1
(58) Field of Search .......................................... 548/377.1

(56) References Cited

U.S. PATENT DOCUMENTS 5,466,823 * 11/1995 Talley et al. ...................... 548/377.1
5,475,018   12/1995 Lee et al. .

FOREIGN PATENT DOCUMENTS

WO 96/37476   11/1996   (WO) .

OTHER PUBLICATIONS

Penning, et al., *J. Med. Chem.*, vol. 40, pp. 1347–1365, 1997.

* cited by examiner

*Primary Examiner*—Robert W Ramsuer
(74) *Attorney, Agent, or Firm*—Raynard Yuro; Richard C. Billups; David L. Rose

(57) ABSTRACT

This invention encompasses a novel process for synthesizing the compound represented by formula I:

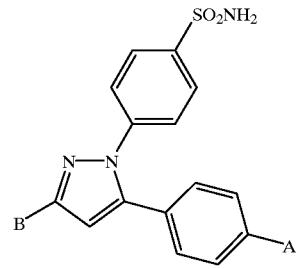

These compounds are useful as non-steroidal anti-inflammatory agents.

2 Claims, No Drawings

SYNTHESIS OF 4-[(5-SUBSTITUTED PHENYL)-3-SUBSTITUTED-1H-PYRAZOL-1-YL]BENZENESULFONAMIDE

CROSS REFERENCE TO RELATED APPLICATIONS

This is a division of application Ser. No. 09/483,564, filed Jan. 14, 2000, now U.S. Pat. No. 6,150,534 which is a non-provisional application related to U.S. application Ser. No. 60/115,834, filed on Jan. 14, 1999 priority of which is claimed hereunder.

BACKGROUND OF THE INVENTION

This application is directed to an improved process for making 4-[5-(4-methylphenyl)-3-(trifluoromethyl)-1H-pyrazol-1-yl]benzenesulfonamide. A general process is disclosed in U.S. Pat. No. 5,466,823 and Penning et al., *J. Med. Chem.*, Vol. 40, pp. 1347–1365, 1997. The process described herein yields a product with a higher ratio of 4-[5-(4-methylphenyl)-3-(trifluoromethyl)-1H-pyrazol-1-yl]benzenesulfonamide with respect to its regioisomer, a higher yield and greater degree of purity than the previously disclosed process. The compound is generally useful as a non-steroidal antiinflammatory agent.

Non-steroidal, antiinflammatory drugs (NSAIDs) exert most of their antiinflammatory, analgesic and antipyretic through an inhibition of prostaglandin G/H synthase, also known as cyclooxygenase. Initially, only one form of cyclooxygenase was known, this corresponding to cyclooxygenase-1 (COX-1) or the constitutive enzyme. More recently, a second inducible form of cyclooxygenase, COX-2, has been characterized. This enzyme is distinct from the COX-1 enzyme. COX-2 is rapidly and readily inducible by a number of agents including mitogens, endotoxin, hormones, cytokines and growth factors. The constitutive enzyme, COX-1, is responsible in large part for endogenous basal release of prostaglandins and hence is important in physiological functions, such as the maintenance of gastrointestinal integrity and renal blood flow. In contrast, COX-2, is mainly responsible for the pathological effects of prostaglandins where rapid induction of the enzyme would occur in response to such agents as inflammatory agents, hormones, growth factors, and cytokines.

A brief description of the potential utility of cyclooxygenase-2 inhibitors is given in an article by John Vane, *Nature*, Vol. 367, pp. 215–216, 1994, and in an article in *Drug News and Perspectives*, Vol. 7, pp. 501–512, 1994.

Thus, one object of the present invention is to provide a process that yields a product with a higher ratio of 4-[5-(4-methylphenyl)-3-(trifluoromethyl)-1H-pyrazol-1-yl]benzenesulfonamide with respect to its regioisomer.

Another object of the present invention is to provide a process with a higher yield and greater degree of purity. These and other objects will be apparent to those of ordinary skill from the teachings contained herein.

SUMMARY OF THE INVENTION

This invention encompasses a novel process for synthesizing the compound represented by formula I:

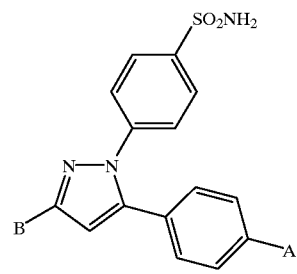

or a salt, hydrate or solvate thereof, wherein A represents H, halo, or methyl, and B represents $CH_3$, $CH_2F$, $CHF_2$ or $CF_3$, comprising reacting a compound of formula II:

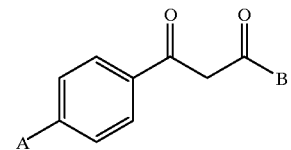

with a compound of formula III:

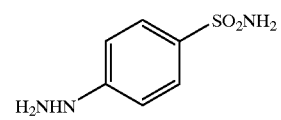

or a salt or hydrate thereof, in an amide solvent at a controlled temperature to produce a compound of formula I.

DETAILED DESCRIPTION OF THE INVENTION

This invention encompasses a novel process for synthesizing a compound represented by formula I:

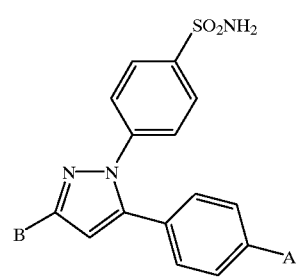

or a salt, hydrate or solvate thereof, wherein A represents H, halo, or methyl, and B represents $CH_3$, $CH_2F$, $CHF_2$ or $CF_3$, comprising reacting a compound of formula II:

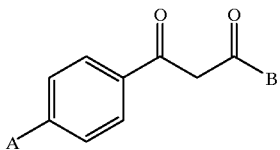

with a compound of formula III:

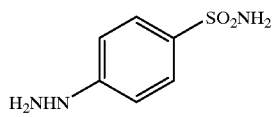

or a salt or hydrate thereof, in an amide solvent at a controlled temperature to produce a compound of formula I.

In a preferred embodiment, the amide solvent is selected from N,N-dimethylformamide, N,N-dimethylacetamide, 1-methyl-2-pyrrolidinone, 1,3-dimethyl-3,4,5,6-tetrahydro-2(1H)-pyrimidinone and 1,1,3,3-tetramethylurea.

In another embodiment, the controlled temperature does not exceed about 30° C.

In yet another embodiment, the amount of the regioisomer of formula I in the product is about 0.5% or less, and the product yield is at least about 80%.

A preferred embodiment is that wherein the compound of formula I is about 99% pure.

Of particular interest are compounds of formula I produced as a solvate of the amide solvent. More particluarly, this invention encompasses recrystallizing the amide solvate of the compound of formula I from isopropanol and water to produce an unsolvated compound of formula I.

For the purposes of this specification, the term "amide solvent" refers to N,N-dimethylformamide, N,N-dimethylacetamide as well as the other solvents that are described above. Ethereal solvents are disclosed in some of the examples and tables for comparison purposes.

The term "controlled temperature" means a threshold reaction temperature under which the reaction temperature is mainatined. An example of a controlled temperature is about 30° C.

The term regioisomer refers to the following structure:

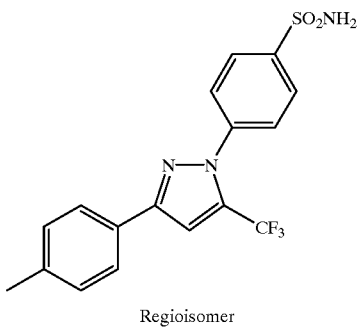

Regioisomer

The points of attachment of the $CF_3$ group and the 4-B-phenyl group on the pyrazole ring are reversed.

The invention is further illustrated by the following non-limiting examples:

Preparative Example 1

4,4,4-Trifluoro-1-(4-methylphenyl)-butane-1,3-dione

Under nitrogen, to a 100 L three-necked round bottom flask equipped with a mechanical stirrer, a nitrogen inlet and a thermocouple charge lithium hexamethyldisilazide (LHMDS) and tetrahydrofuran (THF) (25.0 l, KF=80) at −60° C. Add 4-methylacetophenone over 30 min. Age the mixture at −60° C. for 30 min. Add 2,2,2-trifluroroethyl trifluoroacetate over 30 min, maintaining the temperature at lower than −50° C. during the additions. Age the mixture for 20 hrs at ambient temperature.

Allow the mixture to come to 0° C. Add 3N HCl slowly so that the temperature is maintained at less than 20° C. Age the mixture for 30 min. Separate in the separatory cylinder (100 L) give the THF layer. Concentrate and switch solvents to acetonitrile (ACN). Add ACN to a volume of 12 L. Cool the solution to −10° C. Add $H_2O$ (8.0 L).

Slowly add additional $H_2O$ (45.0 L). Age the mixture at ambient temperature for 3 hrs. Isolate the solid by filtration via an insulated sintered funnel. Rinse the wet cake with $H_2O$ (20.0 L). Dry under reduced pressure to afford 3.68 kg (approx) of the product at 86% yield.

EXAMPLE 1

4-[5-(4-METHYLPHENYL)-3-(TRIFLUOROMETHYL)-1H-PYRAZOL-1-YL] BENZENESULFONAMIDE

Step 1

4-[5-(4-methylphenyl)-3-(trifluoromethyl)-1H-pyrazol-1-yl]benzenesulfonamide.DMAC Under nitrogen, to a 100 L three-necked round bottom flask equipped with a mechanical stirrer, a nitrogen inlet and a thermocouple, charge 4,4,4-trifluoro-1-(4-methylphenyl)-butane-1,3-dione (2.0 kg), 4-sulphonamidophenylhydrazine hydrochloride (1.943 kg) and N,N-dimethylacetamide (DMAC) (40.0 L) at ambient temperature. Slowly add HCl (12 N) (0.36 L) over 30 min. Age the mixture at ambient temperature for 24 hrs. Slowly add $H_2O$ (40.0 L) over 20 min. Age the mixture for 20 hrs at ambient temperature. Keep the reaction temperature under 30° C. The addition of $H_2O$ is slightly exothermic and the temperature should be controlled under 30° C. during the addition. Isolate the solid by filtration via an insulated sintered funnel. Rinse the wet cake with cold DMAC and water (10–12 L).

Step 2

4-[5-(4-methylphenyl)-3-(trifluoromethyl)-1H-pyrazol-1-yl]benzenesulfonamide

Under nitrogen, to a 100 L three-necked round bottom flask equipped with a mechanical stirrer, a nitrogen inlet and a thermocouple charge 4-[5-(4-methylphenyl)-3-(trifluoromethyl)-1H-pyrazol-1-yl] benzenesulfonamide.DMAC (3.3kg) and isopropanol (IPA) (24 L). Heat the mixture to 50° C. Transfer the solution to another 100 L vessel via a pump going through a 1 micron filter to remove insoluble particles. Rinse with more IPA (2.4 L). Slowly add $H_2O$ (39.6 L) over 130 min. Age for 2 hrs at ambient temperature. Isolate the solid by filtration. Wash the cake two times with IPA/water (1:1.5) and two times with water. Dry at 45° C. for 96 hrs. The yield is approximately 2.7 kg (89.6%).

Comparative Example 2

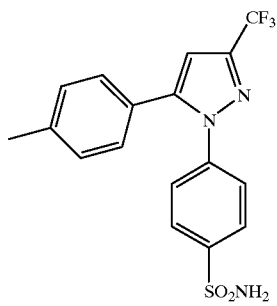

In a 250 ml round bottom flask combine 1-(4-methylphenyl)-4,4,4-trifluorobutane-1,3-dione (3.68 g, 16 mmol), 4-sulfonamidophenylhydrazine hydrochloride (3.58 g, 16 mmol), MTBE (9 ml), methanol (2.5 ml), ethanol (100 ml) and 4N HCl (4.0 ml, 16 mmol). Heat the mixture to reflux for 3 hours. A sample assayed by HPLC shows 2.6 A % of regioisomer. The mixture is cooled, and concentrated under vacuum to 60 ml. Water (30 ml) is added dropwise, during which the product crystallizes. The mixture is aged for 1 hour at room temperature, filtered, washed with ethanol/water (20 ml 60% ethanol, v/v), and water (20 ml). The solid is dried under vacuum at 45° C.

Yield, 4.7 g (76.4%).

HPLC assay 99.1 wt %, with 0.57 A % regioisomer.

MP. 160.5–162.3° C.

EXAMPLE 3

In a 100 ml round bottomed flask combine 1-(4-methylphenyl)-4,4,4-trifluorobutane-1,3-dione (2 g, 8.68 mmol), 4-sulfonamidophenylhydrazine hydrochloride (1.95 g, 8.68 mmol), DMPU (40 ml), 6N HCl (1.4 ml, 8.68 mmol). Stir the mixture for ~16 hours at ambient temperature. A sample assayed by HPLC shows 0.16 A % of regioisomer. Water (40 ml) is added dropwise, during which the product crystallizes. The mixture is aged for ~4 hours at room temperature, filtered, washed with DMPU/water (10 ml, 1:1 v/v), and water (20 ml). The solid is dried under vacuum at 45° C.

Yield, 3.7 g 1:1 DMPU solvate, 2.76 assay g (83%).

HPLC assay 74.8 wt %, with 0.04 A % regioisomer.

MP. 145–146° C.

EXAMPLE 4

In a 100 ml round bottomed flask combine 1-(4-methylphenyl)-4,4,4-trifluorobutane-1,3-dione (2 g, 8.68 mmol), 4-sulfonamidophenylhydrazine hydrochloride (1.95 g, 8.68 mmol), NMP (40 ml), 6N HCl (1.4 ml, 8.68 mmol). Stir the mixture for ~16 hours at ambient temperature. A sample assayed by HPLC shows 0.27 A % of regioisomer. Water (40 ml) is added dropwise, during which the product crystallizes. The mixture is aged for ~4 hours at room temperature, filtered, washed with DMPU/water (10 ml, 1:1 v/v), and water (20 ml). The solid is dried under vacuum at 45° C.

Yield, 3.5 g 1:1 NMP solvate, 2.8 assay g (85%).

HPLC assay 80 wt %, with 0.03 A % regioisomer.

MP. 137–139° C.

EXAMPLE 5

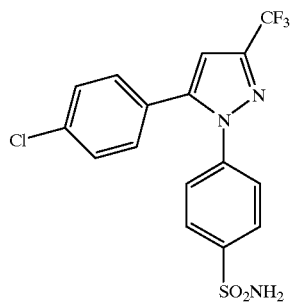

In a 100 ml round bottomed flask combine 1-(4-chlorophenyl)-4,4,4-trifluorobutane-1,3-dione (1.0 g, 3.98 mmol), 4-sulfonamidophenylhydrazine hydrochloride (0.89, 3.98 mmol), DMAc (20 ml), 6N HCl (0.64 ml, 3.98 mmol). Stir the mixture for ~16 hours at ambient temperature. A sample assayed by HPLC shows 0.49 A % of regioisomer. Water (20 ml) is added dropwise, during which the product crystallizes. The mixture is aged for ~4 hours at room temperature, filtered, washed with DMAc/water (5 ml, 1:1 v/v), and water (20 ml). The solid is dried under vacuum at 45° C.

Yield, 1.56 g 1:1 DMAc solvate, (80%).

HPLC assay 0.07 A % regioisomer.

MP. 141.5–143.5° C.

EXAMPLE 6

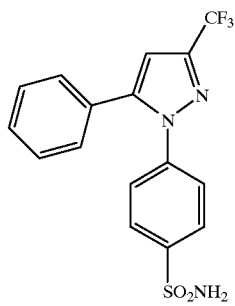

In a 100 ml round bottomed flask combine 1-(phenyl)-4,4,4-trifluorobutane-1,3-dione (2.0 g, 12.3 mmol), 4-sulfonamidophenylhydrazine hydrochloride (2.7 g, 12.3 mmol), DMAc (40 ml), 6N HCl (2.0 ml, 12.3 mmol). Stir the mixture for ~16 hours at ambient temperature. Water (40 ml) is added dropwise, during which the product crystallizes. The mixture is aged for ~4 hours at room temperature, filtered, washed with DMAc/water (10 ml 1:1 v/v), and water 20 ml. The solid is dried under vacuum at 45° C.

Yield, 3.8 g 1:1 DMAc solvate, (85.3%).

HPLC assay 0.07 A % regioisomer.

MP. 113–115° C.

EXAMPLE 7

In a 100 ml round bottomed flask combine 1-(4-chlorophenyl)-4,4-difluorobutane-1,3-dione (1.0 g, 3.98 mmol), 4-sulfonamidophenylhydrazine hydrochloride (0.89, 3.98 mmol), DMAc (20 ml), 6N HCl (0.64 ml, 3.98 mmol). Stir the mixture for ~16 hours at ambient temperature. A sample assayed by HPLC shows 1.16 A % of regioisomer. Water (20 ml) is added dropwise, during which the product crystallizes. The mixture is aged for ~4 hours at room temperature, filtered, washed with DMAc/water (5 ml, 1:1 v/v), and water (20 ml). The solid is dried under vacuum at 45° C.

Yield, 1.9 g 1:1 DMAc solvate, 94(80%).

HPLC assay 0.03 A % regioisomer.

MP. 133–135° C.

Compounds can be prepared in accordance with the procedures described in the examples, using the solvents disclosed in Table 1, and the yields and level of purity relative to the regioisomers are as described below.

TABLE 1

| A | B | Solvent | Solvate | A % regio* | MP ° C. | Yield % |
|---|---|---------|---------|------------|---------|---------|
| $CH_3$ | $CF_3$ | DMAc | 1:1 | 0.02 | 148–149.5 | 83 |
| $CH_3$ | $CF_3$ | DMF | 1:1 | — | 129–131 | 84 |
| $CH_3$ | $CF_3$ | NMP | 1:1 | 0.03 | 137–139 | 85 |
| $CH_3$ | $CF_3$ | DMPU | 1:1 | 0.04 | 145–146 | 83 |
| $CH_3$ | $CF_3$ | TMU | 1:1 | 0.06 | 105–107 | 79 |
| $CH_3$ | $CF_3$ | Ethanol | — | 0.57 | 160.5–162.3 | 76.4 |
| H | $CF_3$ | DMAc | 1:1 | 0.07 | 113–115 | 85.3 |
| H | $CF_3$ | DMF | — | 0.18 | 164–165.5 | 80 |
| Cl | $CF_3$ | DMAc | 1:1 | 0.07 | 141.5–143.5 | 80 |
| Cl | $CF_3$ | DMF | 1:1 | 0.18 | 92.5–93.5 | 79 |
| Cl | $CHF_2$ | DMAc | 1:1 | 0.03 | 133–135 | 94 |
| Cl | $CHF_2$ | DMF | — | 0.03 | 187–189 | 80 |

MTBE = methyl t-butyl ether
DMAc = N,N-Dimethyl-acetamide
DMF = N,N-Dimethyl-formamide
NMP = 1-Methyl-2-pyrrolidinone
DMPU = 1,3-Dimethyl-3,4,5,6-tetrahydro-2(1H)-pyrimidinone
TMU = 1,1,3,3-Tetramethylurea
*= As measured by HPLC

What is claimed:

1. A compound of the following formula:

as a solvate of DMPU, NMP, DMAc, TMU or DMF.

2. A compound in accordance with claim 1 as a 1:1 solvate.

* * * * *